(12) United States Patent
Nakamura

(10) Patent No.: US 12,387,054 B2
(45) Date of Patent: Aug. 12, 2025

(54) INFORMATION SAVING APPARATUS, METHOD, AND PROGRAM AND ANALYSIS RECORD GENERATION APPARATUS, METHOD, AND PROGRAM FOR RECOGNIZING CORRECTION MADE IN IMAGE ANALYSIS RECORD

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 516 days.

(21) Appl. No.: 17/890,270

(22) Filed: Aug. 18, 2022

(65) Prior Publication Data

US 2022/0391599 A1 Dec. 8, 2022

Related U.S. Application Data

(63) Continuation of application No. PCT/JP2021/007977, filed on Mar. 2, 2021.

(30) Foreign Application Priority Data

Mar. 3, 2020 (JP) .................................. 2020-035800

(51) Int. Cl.
 *G06F 40/40* (2020.01)
 *G16H 10/60* (2018.01)
 *G16H 30/40* (2018.01)

(52) U.S. Cl.
 CPC ............. *G06F 40/40* (2020.01); *G16H 10/60* (2018.01); *G16H 30/40* (2018.01)

(58) Field of Classification Search
 None
 See application file for complete search history.

(56) References Cited

U.S. PATENT DOCUMENTS

| 5,807,256 A * | 9/1998 | Taguchi .................... G06T 7/11 600/300 |
| 2005/0107690 A1 * | 5/2005 | Soejima ................. G16H 30/20 600/425 |
| 2007/0083396 A1 | 4/2007 | Kanada et al. |

(Continued)

FOREIGN PATENT DOCUMENTS

| JP | H0731591 | 2/1995 |
| JP | 2007122679 | 5/2007 |

(Continued)

OTHER PUBLICATIONS

"Office Action of Japan Counterpart Application", issued on Oct. 17, 2023, with English translation thereof, p. 1-p. 7.

(Continued)

*Primary Examiner* — Miya J Cato
(74) *Attorney, Agent, or Firm* — JCIPRNET

(57) ABSTRACT

An information saving apparatus includes at least one processor, in which the processor is configured to analyze an image to derive a plurality of pieces of property information indicating properties of a structure of interest included in the image, generate an image analysis record including at least a portion of the plurality of pieces of property information, receive a correction of the property information by a user, and save the derived property information and the corrected property information in a distinguishable manner.

19 Claims, 13 Drawing Sheets

(56) References Cited

U.S. PATENT DOCUMENTS

| | | | |
|---|---|---|---|
| 2010/0189366 A1 | 7/2010 | Iizuka et al. | |
| 2013/0315456 A1* | 11/2013 | Marugame | G06T 7/0012 382/128 |
| 2019/0267132 A1 | 8/2019 | Fuchigami et al. | |
| 2019/0279751 A1 | 9/2019 | Nakamura et al. | |
| 2020/0160993 A1* | 5/2020 | Xie | G06T 7/0012 |
| 2020/0410678 A1* | 12/2020 | Song | G06N 3/08 |

FOREIGN PATENT DOCUMENTS

| | | |
|---|---|---|
| JP | 2009082443 | 4/2009 |
| JP | 2009259000 | 11/2009 |
| JP | 2011125402 | 6/2011 |
| JP | 2016040688 | 3/2016 |
| JP | 2017068801 | 4/2017 |
| JP | 2018110040 | 7/2018 |
| JP | 2019149130 | 9/2019 |
| JP | 2019153250 | 9/2019 |

OTHER PUBLICATIONS

"International Search Report (Form PCT/ISA/210) of PCT/JP2021/007977," mailed on Jun. 8, 2021, with English translation thereof, pp. 1-5.

"Written Opinion of the International Searching Authority (Form PCT/ISA/237)" of PCT/JP2021/007977, mailed on Jun. 8, 2021, with English translation thereof, pp. 1-6.

"Office Action of Japan Counterpart Application", issued on Jan. 7, 2025, with English translation thereof, p. 1-p. 8.

* cited by examiner

LOCATION OF ABNORMAL SHADOW : UNDER LEFT LUNG PLEURA

SIZE OF ABNORMAL SHADOW : 4.2 cm

SHAPE OF BOUNDARY : IRREGULAR

ABSORPTION VALUE : SOLID

SPICULA : −

TUMOR

PLEURAL CONTACT : +

PLEURAL INVAGINATION : +

PLEURAL INFILTRATION : −

CAVITY : −

CALCIFICATION : −

INFORMATION SAVING APPARATUS, METHOD, AND PROGRAM AND ANALYSIS RECORD GENERATION APPARATUS, METHOD, AND PROGRAM FOR RECOGNIZING CORRECTION MADE IN IMAGE ANALYSIS RECORD

CROSS REFERENCE TO RELATED APPLICATIONS

The present application is a Continuation of PCT International Application No. PCT/JP2021/007977, filed on Mar. 2, 2021, which claims priority to Japanese Patent Application No. 2020-035800, filed on Mar. 3, 2020. Each application above is hereby expressly incorporated by reference, in its entirety, into the present application.

BACKGROUND

Technical Field

The present disclosure relates to an information saving apparatus, method, and program and an analysis record generation apparatus, method, and program.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately analyzed by image diagnosis using CT images, MRI images, and the like, appropriate treatment is being performed based on the analyzed result.

In addition, image diagnosis is also made by analyzing a medical image via computer-aided diagnosis (CAD) using a learning model in which machine learning is performed by deep learning or the like, discriminating properties such as the shape, density, position, and size of structures of interest such as abnormal shadow candidates included in the medical images, and acquiring them as an analysis result. The analysis result acquired by CAD is associated with examination information such as a patient name, gender, age, and a modality that has acquired the medical image, and is saved in a database. The medical image and the analysis result are transmitted to a terminal of a radiologist who interprets the medical images. The radiologist interprets the medical image by referring to the transmitted medical image and analysis result and creates an interpretation report, in his or her own terminal.

Meanwhile, with the improvement of the performance of the CT apparatus and the MRI apparatus described above, the number of medical images to be interpreted is also increasing. However, since the number of radiologists has not kept up with the number of medical images, it is desired to reduce the burden of the image interpretation work of the radiologists. Therefore, various methods have been proposed to support the creation of medical documents such as interpretation reports. For example, JP2019-153250A proposes a method for automatically generating a sentence to be included in an interpretation report based on keywords input by a radiologist and on information indicating a property of a structure of interest (hereinafter referred to as property information) included in an analysis result of a medical image. In the methods described in JP2019-153250A, a sentence relating to medical care (hereinafter referred to as a medical sentence) is created by using a learning model in which machine learning is performed, such as a recurrent neural network trained to generate a sentence from characters representing the input property information. By automatically generating the medical sentence as in the method described in JP2019-153250A, it is possible to reduce a burden on a radiologist at the time of creating a medical document such as an interpretation report.

Incidentally, the automatically generated interpretation report may be corrected by the radiologist. In addition, in the case of comparing with time, in describing the latest medical image interpretation report, the past medical image interpretation report is often referred to. Therefore, a method of extracting the corrected part of the corrected interpretation report (see JP2011-125402A) and a method of extracting the difference between the past medical image interpretation report and the latest medical image interpretation report (see JP2007-122679A) have been proposed.

In a learning model that generates an image analysis record such as a sentence from an image, such as a learning model that generates an interpretation report from a medical image, there is a user's preference for the content and expression of the analysis record, and it is desired to construct a learning model that reflects that preference. As the user's preference, for example, regarding property information analyzed from the image, which property information should be reflected in the final analysis record and the like can be mentioned.

However, depending on the content of supervised training data used to train the learning model, or depending on the learning limits of the learning model, the generated image analysis record may not match the user's preference. In such cases, the user needs to correct the generated image analysis record. Here, in a case where the image analysis record is a sentence, if the sentences before and after the correction are compared using the methods described in JP2011-125402A and JP2007-122679A, it is possible to recognize which part of the sentence has been corrected.

However, in the case of the methods described in JP2011-125402A and JP2007-122679A, although the corrected part of the image analysis record can be known, it is not possible to recognize which of the property information acquired by analyzing the image has been corrected. Since the learning model generates an image analysis record from the property information, it is difficult to construct a learning model according to the user's preference unless it is known which of the property information has been corrected.

SUMMARY OF THE INVENTION

The present disclosure has been made in view of the above circumstances, and an object thereof is to be able to recognize which of property information derived by analyzing an image has been corrected in a case where an image analysis record generated from the image has been corrected.

According to an aspect of the present disclosure, there is provided an information saving apparatus comprising at least one processor, in which the processor is configured to analyze an image to derive a plurality of pieces of property information indicating properties of a structure of interest included in the image, generate an image analysis record including at least a portion of the plurality of pieces of property information, receive a correction of the property information by a user, and save the derived property information and the corrected property information in a distinguishable manner.

In the information saving apparatus according to the aspect of the present disclosure, the processor may be configured to display the image analysis record on the display.

In the information saving apparatus according to the aspect of the present disclosure, the processor may be configured to receive at least one of deletion of the property information included in the displayed image analysis record or addition of the property information not included in the image analysis record as the correction.

In the information saving apparatus according to the aspect of the present disclosure, the processor may display an entirety or a portion of the derived property information on the display, and receive the correction based on selection of the displayed property information by the user.

The information saving apparatus according to the aspect of the present disclosure may further comprise a learning model trained to output the image analysis record in a case where the property information is input.

In the information saving apparatus according to the aspect of the present disclosure, the processor may be configured to generate a sentence including at least a portion of the property information as the image analysis record.

In the information saving apparatus according to the aspect of the present disclosure, the image may be a medical image, and the sentence may be a medical sentence related to the structure of interest included in the medical image.

According to another aspect of the present disclosure, there is provided an analysis record generation apparatus comprising at least one processor, in which the processor is configured to derive a plurality of pieces of property information indicating properties of a structure of interest included in a target image to be analyzed, and refer to the information saved by the information saving apparatus according to the aspect of the present disclosure to generate a target image analysis record including at least a portion of the property information.

In the analysis record generation apparatus according to the aspect of the present disclosure, the processor may be configured to specify the saved information including property information that matches the property information derived from the target image, and generate an image analysis record associated with the specified saved information as the target image analysis record.

In the analysis record generation apparatus according to the aspect of the present disclosure, the processor may be further configured to generate another target image analysis record including at least a portion of the derived property information without reference to the saved information.

The expression "to generate another target image analysis record . . . , without reference to . . . " means to generate another target image analysis record without referring to the saved information.

In the analysis record generation apparatus according to the aspect of the present disclosure, the processor may be configured to display the target image analysis record and the other target image analysis record on a display.

In the analysis record generation apparatus according to the aspect of the present disclosure, the processor may be configured to receive selection of either the displayed target image analysis record or the displayed other target image analysis record.

In the analysis record generation apparatus according to the aspect of the present disclosure, the processor may be configured to generate a sentence including at least a portion of the property information as the target image analysis record.

In the analysis record generation apparatus according to the aspect of the present disclosure, the image may be a medical image, and the sentence may be a medical sentence related to the structure of interest included in the medical image.

According to another aspect of the present disclosure, there is provided an information saving method comprising: analyzing an image to derive a plurality of pieces of property information indicating properties of a structure of interest included in the image; generating an image analysis record including at least a portion of the plurality of pieces of property information; receiving a correction of the property information by a user; and saving the derived property information and the corrected property information in a distinguishable manner.

According to another aspect of the present disclosure, there is provided an analysis record generation method comprising: deriving a plurality of pieces of property information indicating properties of a structure of interest included in a target image to be analyzed; and referring to the information saved by the information saving apparatus according to the aspect of the present disclosure to generate a target image analysis record including at least a portion of the property information.

In addition, the information saving method and the analysis record generation method according to the aspects of the present disclosure may be provided as a program for causing a computer to execute the methods.

According to the aspects of the present disclosure, it is possible to recognize which of property information derived by analyzing an image has been corrected in a case where an image analysis record generated from the image has been corrected.

BRIEF DESCRIPTION OF THE DRAWINGS

FIG. 5 is a diagram for describing property information derived by an analysis unit.

DESCRIPTION OF THE PREFERRED EMBODIMENTS

Figure 1:
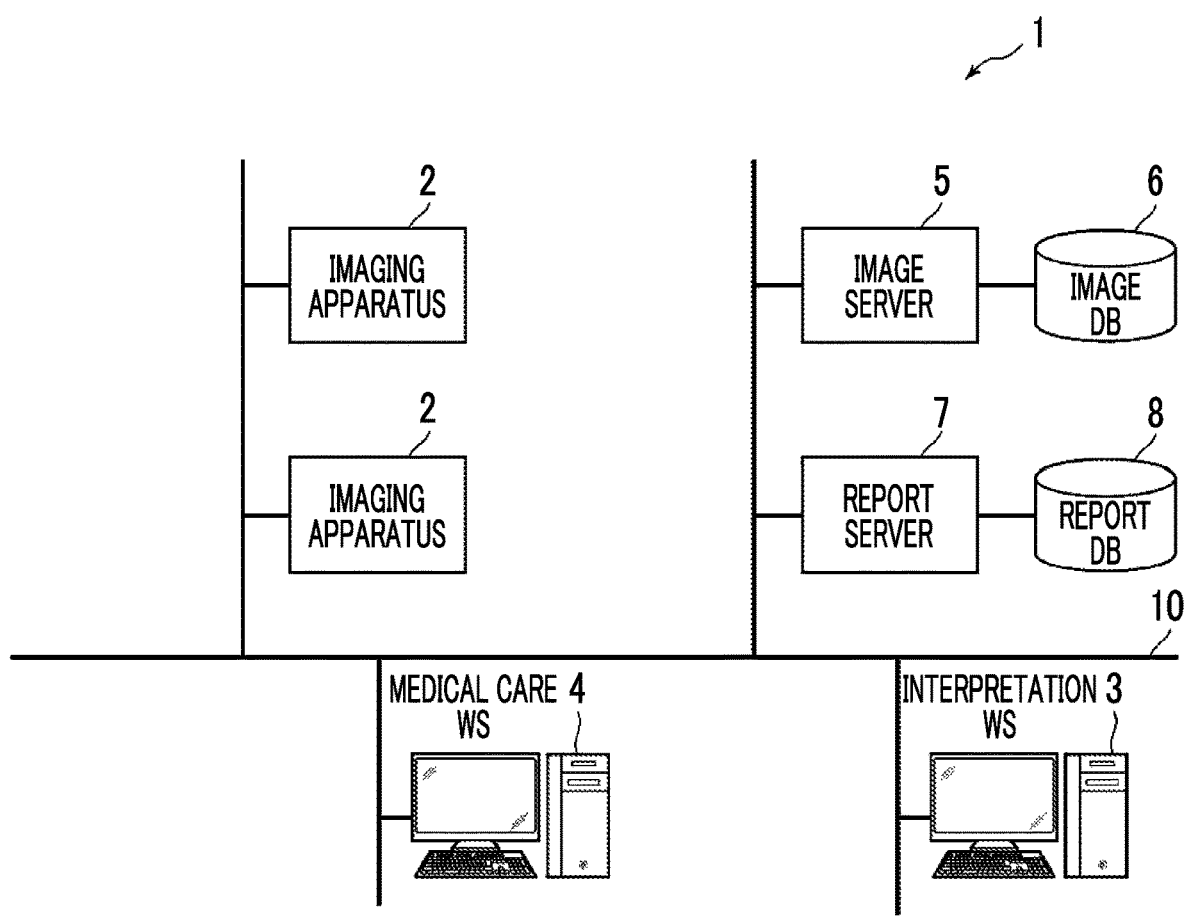
FIG. 1 is a diagram showing a schematic configuration of a medical information system to which an information saving apparatus and an analysis record generation apparatus according to an embodiment of the present disclosure are applied.

Hereinafter, embodiments of the present disclosure will be described with reference to the drawings. First, a configuration of a medical information system 1 to which an information saving apparatus and an analysis record generation apparatus according to the present embodiment are applied will be described. FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, and a report database (hereinafter referred to as a report DB) 8 are communicably connected to each other through a wired or wireless network 10.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 10 or in a network storage in a state in which it can be accessed from the outside, and is downloaded to and installed on the computer in response to a request.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. The medical image generated by the imaging apparatus 2 is transmitted to the image server 5 and is saved in the image DB 6.

The interpretation WS 3 is a computer used by, for example, a radiologist of the radiology department to interpret a medical image and to create an interpretation report, and encompasses an information saving apparatus and an analysis record generation apparatus (hereinafter, represented by the information saving apparatus) 20 according to the present embodiment. In the interpretation WS 3, a viewing request for a medical image to the image server 5, various image processing for the medical image received from the image server 5, display of the medical image, input reception of comments on findings regarding the medical image, and the like are performed. In the interpretation WS 3, an analysis process for medical images and input comments on findings, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, information for accessing a medical image including a specific region, and property information.

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

In the present embodiment, it is assumed that the medical image is a three-dimensional CT image consisting of a plurality of tomographic images with a lung as a diagnosis target, and an interpretation report on an abnormal shadow included in the lung is created as a medical document by interpreting the CT image in the interpretation WS 3. The medical image is not limited to the CT image, and any medical image such as an Mill image and a two-dimensional image acquired by a simple X-ray imaging apparatus can be used.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
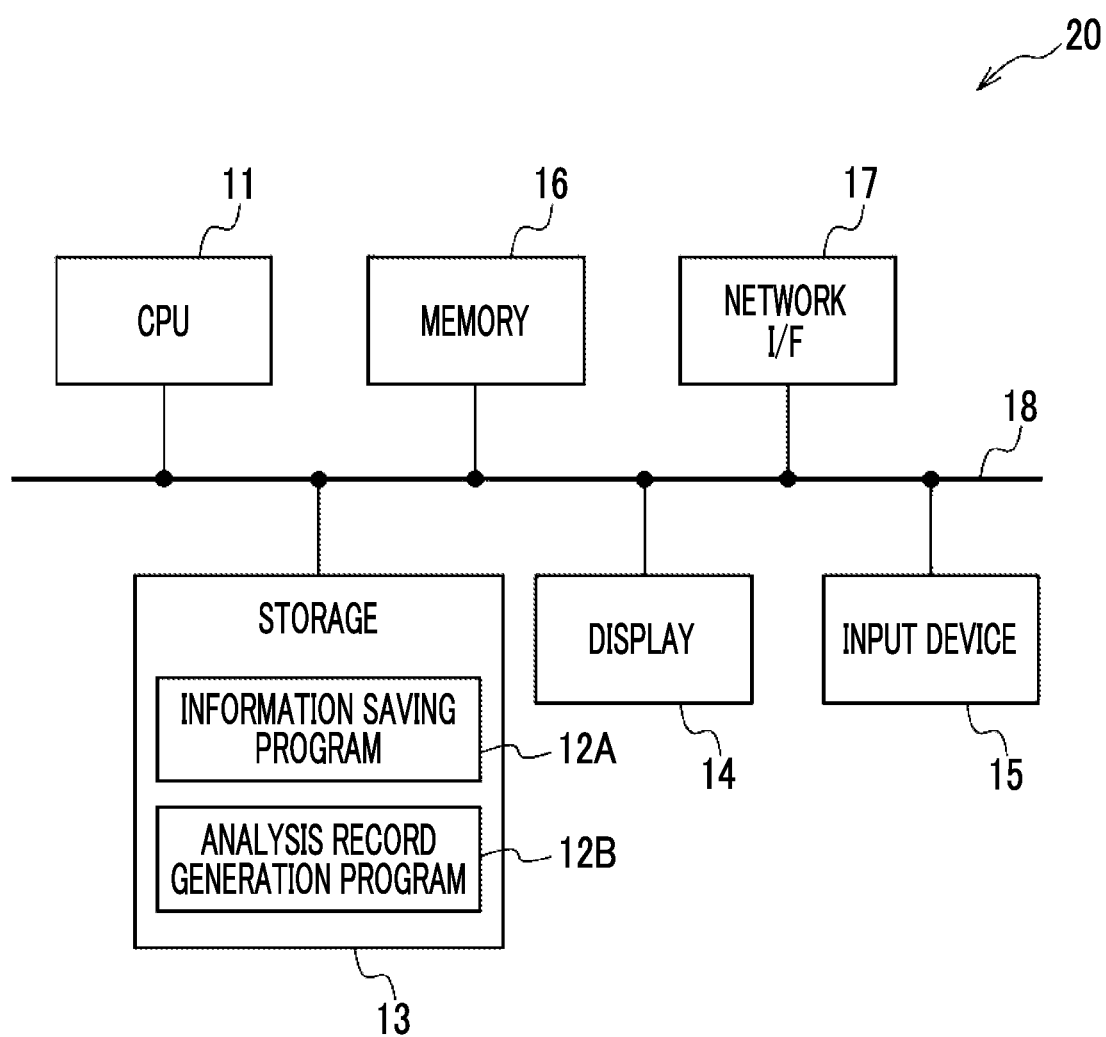
FIG. 2 is a diagram showing a schematic configuration of the information saving apparatus and the analysis record generation apparatus according to the present embodiment.

Next, the information saving apparatus and the analysis record generation apparatus according to the present embodiment will be described. FIG. 2 describes the hardware configuration of the information saving apparatus and the analysis record generation apparatus according to the present embodiment. In FIG. 2, the information saving apparatus 20 represents the information saving apparatus and the analysis record generation apparatus. As shown in FIG. 2, the information saving apparatus 20 includes a central processing unit (CPU) 11, a non-volatile storage 13, and a memory 16 as a temporary storage area. Further, the information saving apparatus 20 includes a display 14 such as a liquid crystal display, an input device 15 such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. An information saving program 12A and an analysis record generation program 12B are stored in the storage 13 as a storage medium. The CPU 11 reads out the information saving program 12A and the analysis record generation program 12B from the storage 13, loads the read-out programs into the memory 16, and executes the loaded information saving program 12A and analysis record generation program 12B.

Figure 3:
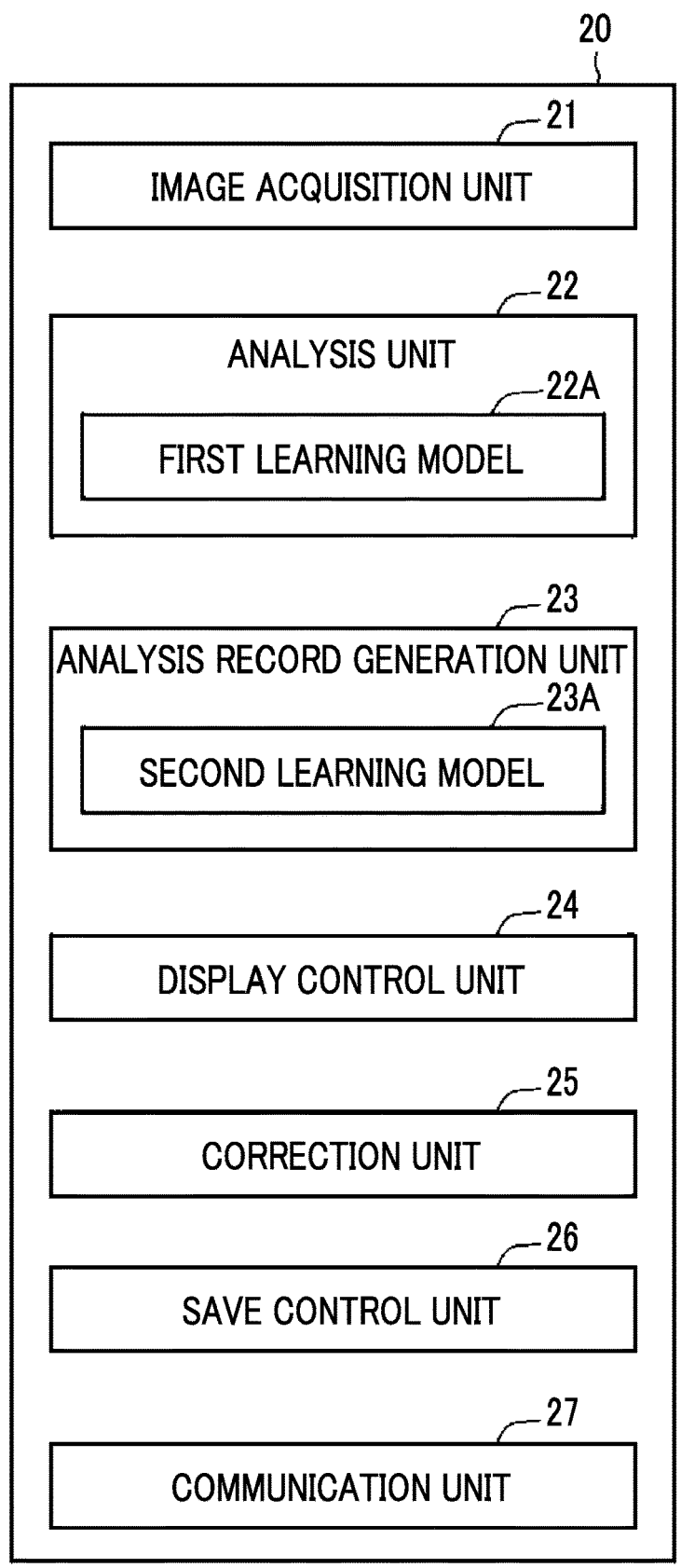
FIG. 3 is a functional configuration diagram of the information saving apparatus and the analysis record generation apparatus according to the present embodiment.

Next, the functional configuration of the information saving apparatus and the analysis record generation apparatus according to the present embodiment will be described. FIG. 3 is a diagram showing the functional configuration of the information saving apparatus and the analysis record generation apparatus according to the present embodiment. As shown in FIG. 3, the information saving apparatus (and analysis record generation apparatus) 20 comprises an image acquisition unit 21, an analysis unit 22, an analysis record generation unit 23, a display control unit 24, a correction unit 25, a save control unit 26, and a communication unit 27. Then, in a case where the CPU 11 executes the information saving program 12A and the analysis record generation program 12B, the CPU 11 functions as the image acquisition unit 21, the analysis unit 22, the analysis record generation unit 23, the display control unit 24, the correction unit 25, the save control unit 26, and the communication unit 27.

In the present embodiment, the image acquisition unit 21, the analysis unit 22, the analysis record generation unit 23, the display control unit 24, and the communication unit 27 have a common configuration in the information saving program 12A and the analysis record generation program 12B.

The image acquisition unit 21 acquires a medical image for creating an interpretation report from the image server 5 according to an instruction from the input device 15 by the radiologist who is an operator. Also, the medical image includes a target medical image to be analyzed, which will be described later.

The analysis unit 22 analyzes the medical image to derive property information indicating the property of the structure of interest such as an abnormal shadow candidate included in the medical image. To this end, the analysis unit 22 has a first learning model 22A in which machine learning is performed so as to discriminate an abnormal shadow candidate in the medical image and to discriminate the property of the discriminated abnormal shadow candidate. In the present embodiment, the first learning model 22A consists of a convolutional neural network (CNN) in which deep learning is performed using supervised training data so as to discriminate whether or not each pixel (voxel) in the medical image represents an abnormal shadow candidate, and to discriminate a property of a pixel in a case where the pixel represents an abnormal shadow candidate.

Figure 4:
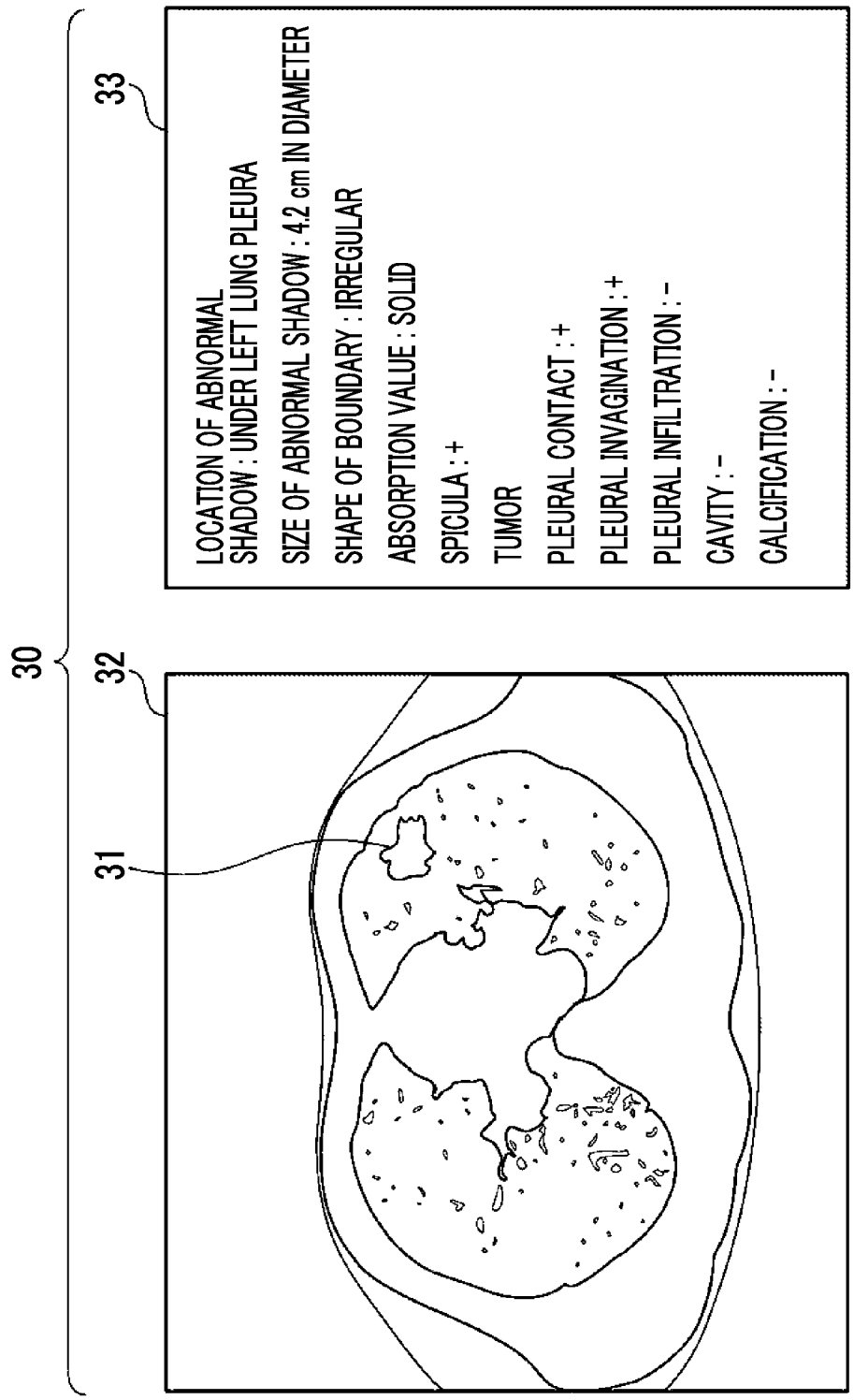
FIG. 4 is a diagram showing an example of supervised training data for training a first learning model.

FIG. 4 is a diagram showing an example of supervised training data for training a first learning model. As shown in FIG. 4, supervised training data 30 includes a medical image 32 including an abnormal shadow 31 and property information 33 about the abnormal shadow. In the present embodiment, it is assumed that the abnormal shadow 31 is a lung nodule, and the property information 33 indicates a plurality of properties of the lung nodule. For example, as the property information 33, the location of the abnormal shadow, the size of the abnormal shadow, the shape of the boundary (clear and irregular), the type of absorption value (solid type and frosted glass type), the presence or absence of spicula, whether it is a tumor or a nodule, the presence or absence of pleural contact, the presence or absence of pleural invagination, the presence or absence of pleural infiltration, the presence or absence of a cavity, and the presence or absence of calcification are used. Regarding the abnormal shadow 31 included in the supervised training data 30 shown in FIG. 4, the property information 33 indicates, as shown in FIG. 4, that the location of the abnormal shadow is under the left lung pleura, the size of the abnormal shadow is 4.2 cm in diameter, the shape of the boundary is irregular, the absorption value is a solid type, spicula is present, it is a tumor, pleural contact is present, pleural invagination is present, pleural infiltration is absent, a cavity is absent, and calcification is absent. In addition, in FIG. 4, + is given in the case of "presence", and − is given in the case of "absence". The first learning model 22A is constructed by training a neural network using a large amount of supervised training data as shown in FIG. 4. For example, by using the supervised training data 30 shown in FIG. 4, the first learning model 22A is trained to discriminate the abnormal shadow 31 included in the medical image 32 in a case where the medical image 32 shown in FIG. 4 is input, and output the property information 33 shown in FIG. 4 with regard to the abnormal shadow 31.

Further, as the first learning model 22A, any learning model such as, for example, a support vector machine (SVM) can be used in addition to the convolutional neural network.

Note that the learning model for detecting the abnormal shadow candidate from the medical image and the learning model for detecting the property information of the abnormal shadow candidate may be constructed separately. Further, the property information derived by the analysis unit 22 is saved in the storage 13. FIG. 5 is a diagram for describing the property information derived by the analysis unit 22. As shown in FIG. 5, the property information 35 derived by the analysis unit 22 is assumed to be "under left lung pleura", "4.2 cm", "irregular", "solid", "no spicula", "tumor", "with pleural contact", "with pleural invagination", "no pleural infiltration", "no cavity", and "no calcification".

Figure 6:
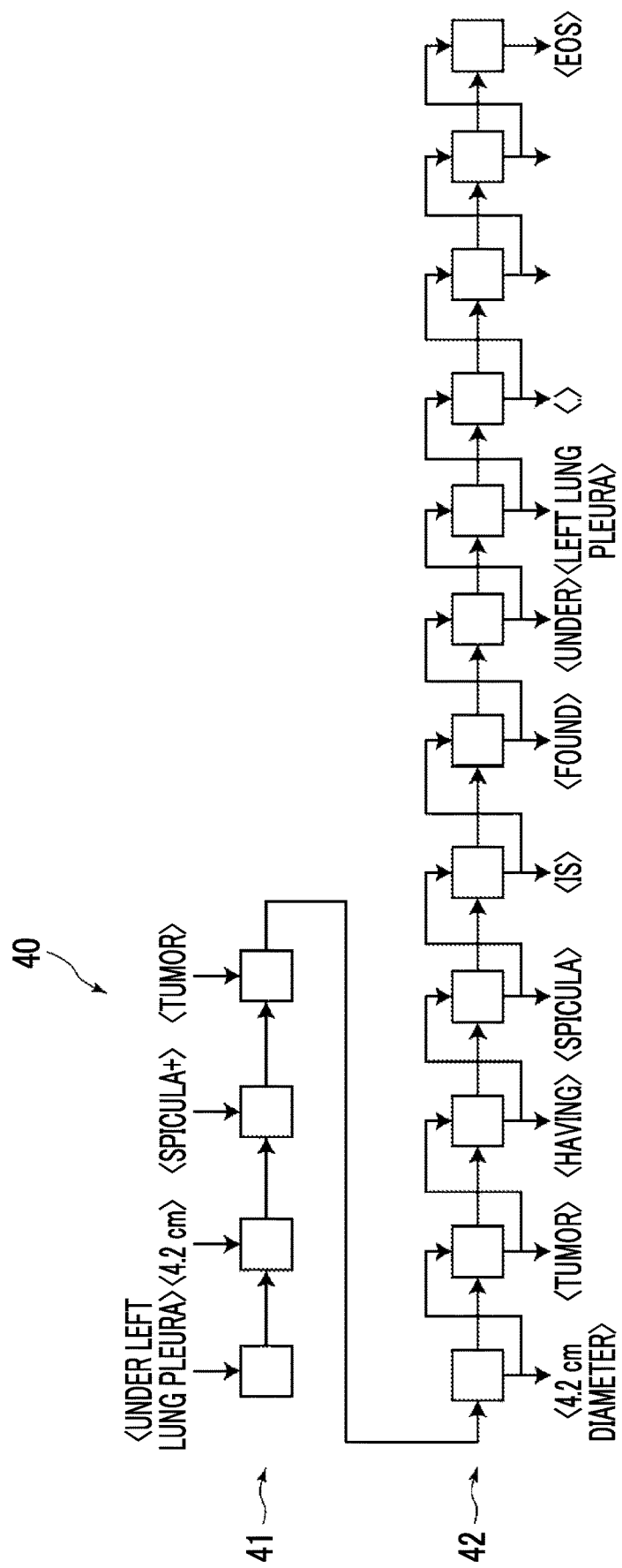
FIG. 6 is a diagram schematically showing a configuration of a recurrent neural network.

The analysis record generation unit 23 generates an image analysis record by using the property information derived by the analysis unit 22. In the present embodiment, a medical sentence is generated as an image analysis record. The analysis record generation unit 23 consists of a second learning model 23A that has been trained to generate a sentence from the input information. As the second learning model 23A, for example, a recurrent neural network can be used. FIG. 6 is a diagram schematically showing a configuration of a recurrent neural network. As shown in FIG. 6, the recurrent neural network 40 consists of an encoder 41 and a decoder 42. The property information derived by the analysis unit 22 is input to the encoder 41. For example, property information indicating "under left lung pleura", "4.2 cm", "spicula +" and "tumor" is input to the encoder 41. The decoder 42 is trained to document character information, and generates a sentence from the input property information. Specifically, from the above-mentioned property information indicating "under left lung pleura", "4.2 cm", "spicula +" and "tumor", a medical sentence "A 4.2 cm diameter tumor having spicula is found under the left lung pleura." is generated. In FIG. 6, "EOS" indicates the end of the sentence (end of sentence).

In this way, in order to output the medical sentence by inputting the property information, the recurrent neural network 40 is constructed by training the encoder 41 and the decoder 42 using a large amount of supervised training data consisting of a combination of the property information and the medical sentence.

Figure 7:
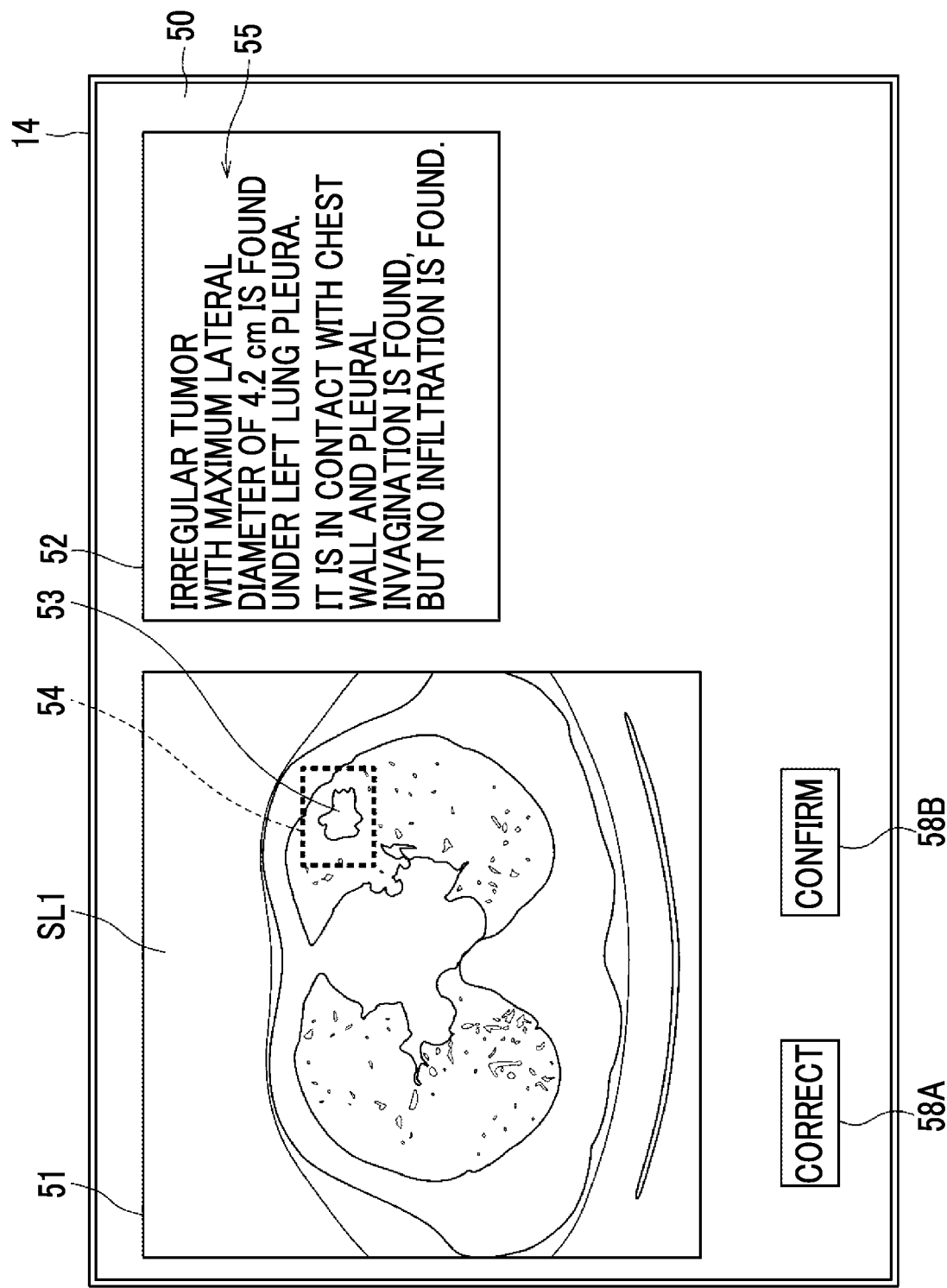
FIG. 7 is a diagram showing an example of a display screen of a medical sentence.

The display control unit 24 displays the medical sentence generated by the analysis record generation unit 23 on the display 14. FIG. 7 is a diagram showing an example of a display screen of a medical sentence according to the present embodiment. As shown in FIG. 7, a display screen 50 includes an image display region 51 and a sentence display region 52. In the image display region 51, a slice image SL1 that is most likely to specify the abnormal shadow candidate detected by the analysis unit 22 is displayed. The slice image SL1 includes an abnormal shadow candidate 53, and the abnormal shadow candidate 53 is surrounded by a rectangular region 54.

In the sentence display region 52, a medical sentence 55 generated by the analysis record generation unit 23 is displayed. The medical sentence 55 is "An irregular tumor with a maximum lateral diameter of 4.2 cm is found under the left lung pleura. It is in contact with the chest wall and pleural invagination is found, but no infiltration is found." The property information used in the medical sentence 55 is "under left lung pleura", "irregular", "4.2 cm", "tumor", "with chest wall contact", "with pleural invagination", and "no pleural infiltration" among the property information derived by the analysis unit 22.

Below the image display region 51, a correction button 58A and a confirmation button 58B are displayed.

The radiologist interprets the abnormal shadow candidate 53 in the slice image SL1 displayed in the image display region 51, and determines the suitability of the medical sentence 55 displayed in the sentence display region 52.

In a case where the radiologist wants to correct the medical sentence 55, he or she uses the input device 15 to select the correction button 58A. Thereby, the correction unit 25 receives corrections by the radiologist for the property information. That is, the medical sentence 55 displayed in the sentence display region 52 can be manually corrected by input from the input device 15. Further, by selecting the confirmation button 58B, the medical sentence 55 displayed in the sentence display region 52 can be confirmed with its contents. In this case, the medical sentence 55 is transcribed in an interpretation report, and the interpretation report to which the medical sentence 55 has been transcribed is transmitted to the report server 7 together with the slice image SL1 and stored therein.

At the time when the radiologist selects the correction button 58A to correct the medical sentence 55, in a case where there is a property that is included in the abnormal shadow 31, but is lacking in the medical sentence 55, the radiologist corrects the medical sentence 55 to add the lacking property. In this case, the radiologist inputs the lacking property using the input device 15. For example, in the present embodiment, it is assumed that spicula is found in the abnormal shadow 31, but the medical sentence 55 lacks the description of spicula. In this case, the radiologist inputs the property information of "spicula" using the input device 15. Thereby, the correction unit 25 corrects the medical sentence 55 to add the property information of "spicula".

In addition, in a case where there is an unnecessary property that is not seen in the medical image in the medical sentence 55, or there is a property that is seen in the medical image but is considered by the radiologist to be unnecessary in the medical sentence 55, the radiologist corrects the medical sentence 55 to delete unnecessary properties. For example, in the present embodiment, in a case where the property of being in contact with the chest wall is unnecessary, the radiologist deletes the property information of "in contact with the chest wall" using the input device 15. Thereby, the correction unit 25 corrects the medical sentence 55 to delete the property information of "in contact with the chest wall".

Figure 8:
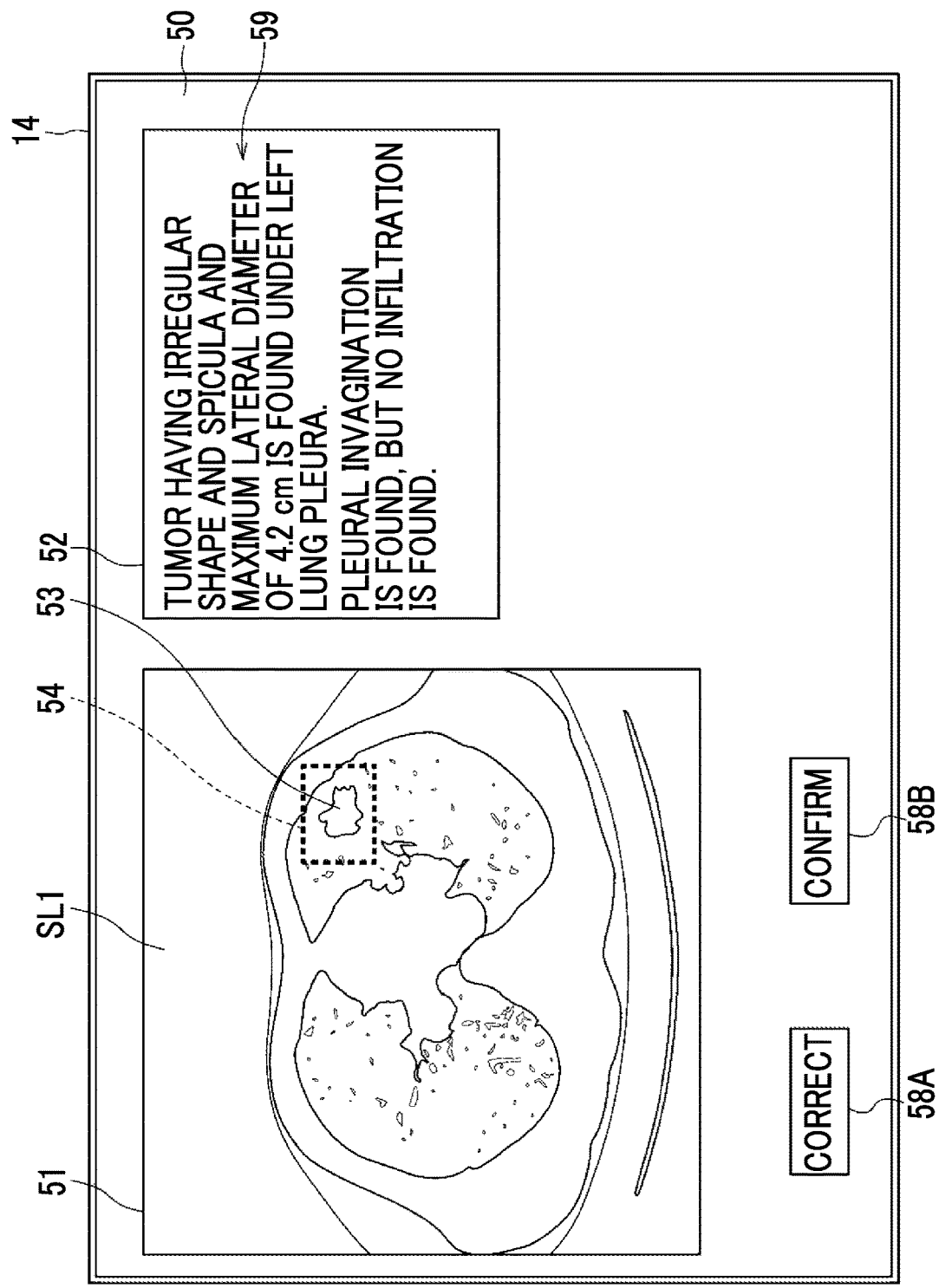
FIG. 8 is a diagram showing an example of a display screen of a corrected medical sentence.

FIG. 8 is a diagram showing an example of a display screen of a corrected medical sentence. As shown in FIG. 8, in a sentence display region 52, a corrected medical sentence 59 obtained by correcting the medical sentence 55 is displayed. The corrected medical sentence 59 is "A tumor having an irregular shape and spicula and a maximum lateral diameter of 4.2 cm is found under the left lung pleura. Pleural invagination is found, but no infiltration is found."

Here, in a case where the medical sentence 55 is corrected as shown in FIG. 8, the property information is corrected so that "no spicula" is corrected to "with spicula" and "with chest wall contact" is corrected to "no chest wall contact".

In a case where the radiologist selects the confirmation button 58B without making corrections, the medical sentence 55 displayed in the sentence display region 52 can be confirmed with its contents. In this case, the medical sentence 55 is transcribed in an interpretation report, and the interpretation report to which the medical sentence 55 has been transcribed is transmitted to the report server 7 through the communication unit 27 together with the slice image SL1 and stored therein. Further, in a case where the radiologist selects the confirmation button 58B after the correction, the corrected medical sentence 59 can be confirmed with its contents. In this case, the corrected medical sentence 59 is transcribed in an interpretation report, and the interpretation report to which the corrected medical sentence 59 has been transcribed is transmitted to the report server 7 through the communication unit 27 together with the slice image SL1 and saved information 45 to be described later and stored therein. In the report server 7, the interpretation report and the saved information 45 are associated and saved.

Figure 9:
FIG. 9 is a diagram for describing saved information showing a saved result of property information.

The save control unit 26 saves the property information derived by the analysis unit 22 and the corrected property information received by the correction unit 25 in the storage 13 in a distinguishable manner. FIG. 9 is a diagram for describing saved information showing a saved result of property information. As shown in FIG. 9, in the property information derived by the analysis unit 22 shown in FIG. 5, the saved information 45 is corrected so that "no spicula" is corrected to "with spicula" and "with chest wall contact" is corrected to "no chest wall contact". In the saved information 45, a flag of +1 is given to the property information corrected from "no" to "with", a flag of −1 is given to the property information corrected from "with" to "no", and a flag of 0 is given to the property information not corrected. As a result, in the saved information 45, the property information derived by the analysis unit 22 and the corrected property information can be distinguished by a flag. The saved information 45 saved in the storage 13 is transmitted to the report server 7 together with the interpretation report and saved therein as described above.

On the other hand, in a case where the image acquisition unit 21 of the information saving apparatus 20 acquires the medical image to be analyzed (hereinafter referred to as the target medical image), the analysis unit 22 analyzes the target medical image to derive the property information of the target medical image. Further, the analysis record generation unit 23 generates a target medical sentence from the property information of the target medical image without reference to the saved information 45 saved in the report server 7, that is, without referring to the saved information 45. Specifically, the analysis record generation unit 23 generates a target medical sentence by using only the property information derived by the analysis unit 22. The target medical sentence without reference to the saved information 45 corresponds to another target image analysis record of the present disclosure. Further, the analysis record generation unit 23 refers to the saved information 45 saved in the report server 7 and generates a target medical sentence as an alternative plan from the property information of the target medical image.

Hereinafter, generation of an alternative plan will be described. First, the analysis record generation unit 23 specifies the saved information 45 including the property information that matches the property information of the target medical image derived by the analysis unit 22 by searching the report server 7. Note that it is assumed that the property information and the saved information 45 include the location and size of the abnormal shadow, but the saved information 45 in which the property items excluding the location and size of the abnormal shadow match is specified. For example, in a case where the property information of the target medical image is "tumor", "with pleural invagination", and "no infiltration", the analysis record generation unit 23 searches for the saved information 45 including the property information of "tumor", "with pleural invagination", and "no infiltration". Then, the analysis record generation unit 23 acquires an interpretation report associated with the saved information 45 that matches the property information of the target medical image from the report server 7.

Here, the fact that the property information matches includes not only the case where all the property information except the location and size of the abnormal shadow among the plurality of pieces of property information matches, but also the case where the majority of the plurality of pieces of property information, for example, 80% or more and even 90% or more of the plurality of pieces of property information match.

In a case where there are a plurality of pieces of saved information 45 that match the property information of the target medical image, it can be selected according to the criteria such as the one with a new creation date or the one created by the radiologist who is operating the interpretation WS 3. Alternatively, the number of interpretation reports to be acquired may be limited to search for saved information that matches the property information. Then, the analysis record generation unit 23 rewrites the location and size of the abnormal shadow in the acquired interpretation report to the location and size of the abnormal shadow included in the property information of the target medical image, and generates an alternative plan. Note that the saved information 45 that matches the property information of the target medical image may not be saved in the report server 7. In such a case, it is assumed that no alternative plan is generated in the present embodiment.

Figure 10:
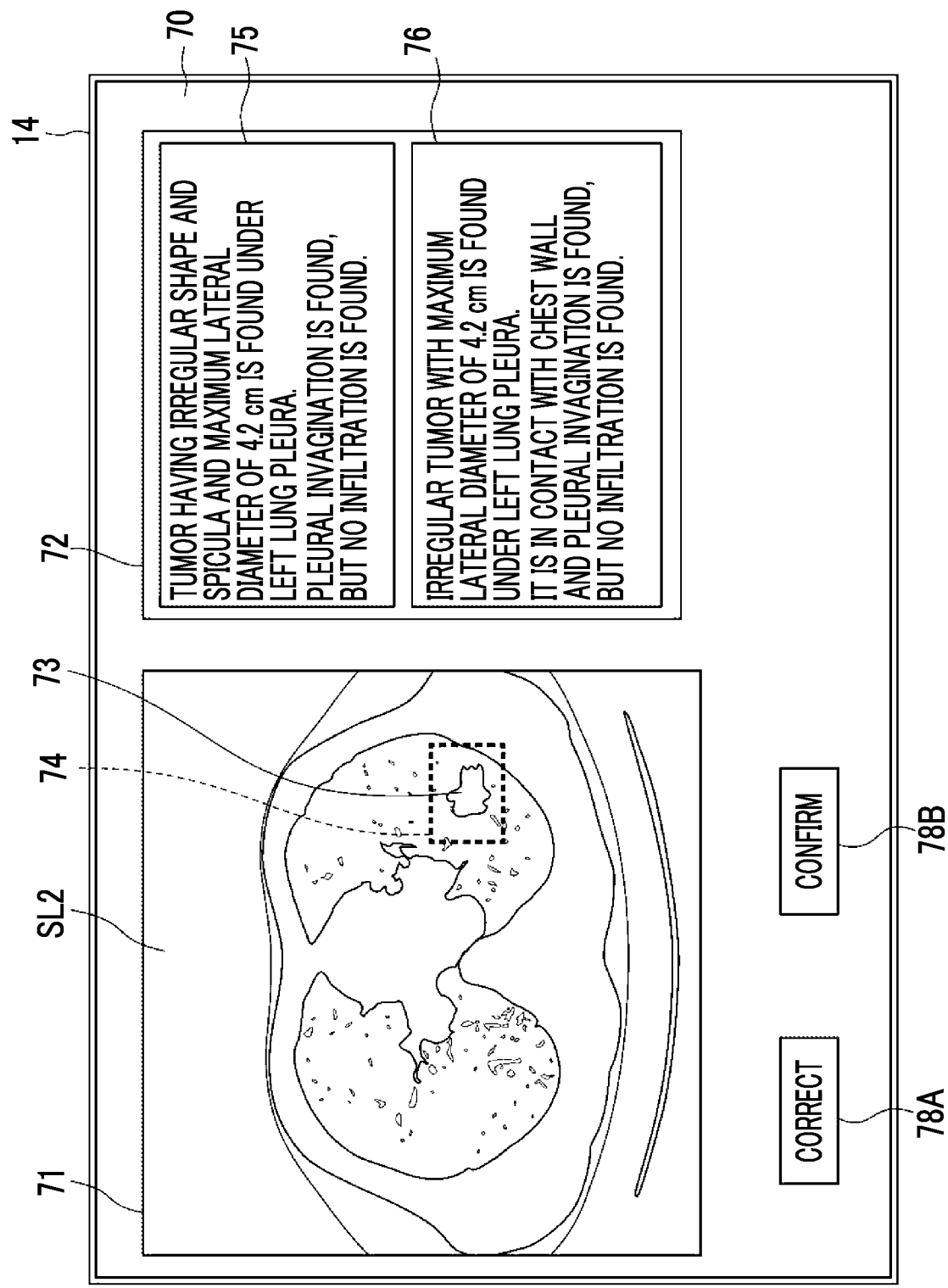
FIG. 10 is a diagram showing an example of a display screen of a target medical sentence and an alternative plan.

The display control unit 24 displays the target medical sentence and an alternative plan of the target medical sentence on the display 14. FIG. 10 is a diagram showing a display screen of a target medical sentence and an alternative plan. Note that FIG. 10 shows only one alternative plan. As shown in FIG. 10, a display screen 70 includes an image display region 71 and a sentence display region 72. In the image display region 71, a slice image SL2 that is most likely to specify the abnormal shadow candidate detected by the analysis unit 22 from the target medical image is displayed. The slice image SL2 includes an abnormal shadow candidate 73, and the abnormal shadow candidate 73 is surrounded by a rectangular region 74.

In the sentence display region 72, a target medical sentence 75 and an alternative plan 76 generated by the analysis record generation unit 23 are displayed. The target medical sentence 75 is "A tumor having an irregular shape and spicula and a maximum lateral diameter of 4.2 cm is found under the left lung pleura. Pleural invagination is found, but no infiltration is found." The alternative plan 76 is "An irregular tumor with a maximum lateral diameter of 4.2 cm is found under the left lung pleura. It is in contact with the chest wall and pleural invagination is found, but no infiltration is found."

Below the image display region 71, a correction button 78A and a confirmation button 78B are displayed.

The radiologist interprets the abnormal shadow candidate 73 in the slice image SL2 displayed in the image display region 71, and determines the suitability of the target medical sentence 75 and the alternative plan 76 displayed in the sentence display region 72.

In a case where the radiologist disagrees with either the target medical sentence 75 or the alternative plan 76 and wants to make corrections, he or she uses the input device 15 to select the correction button 78A. Thereby, the medical sentence 75 displayed in the sentence display region 72 can be corrected in the same manner as described above by input from the input device 15.

On the other hand, in a case where the radiologist adopts either the target medical sentence 75 or the alternative plan 76, the radiologist selects either the target medical sentence 75 or the alternative plan 76 using the input device 15 and selects the confirmation button 78B, thereby confirming either the target medical sentence 75 or the alternative plan 76 with its contents. In this case, any of the selected target medical sentence 75 and alternative plan 76 is transcribed in the interpretation report, and the interpretation report to which the sentence has been transcribed is transmitted to the report server 7 together with the slice image SL2 and stored therein.

The communication unit 27 exchanges information between the information saving apparatus 20 and the external device via the network I/F17.

Figure 11:
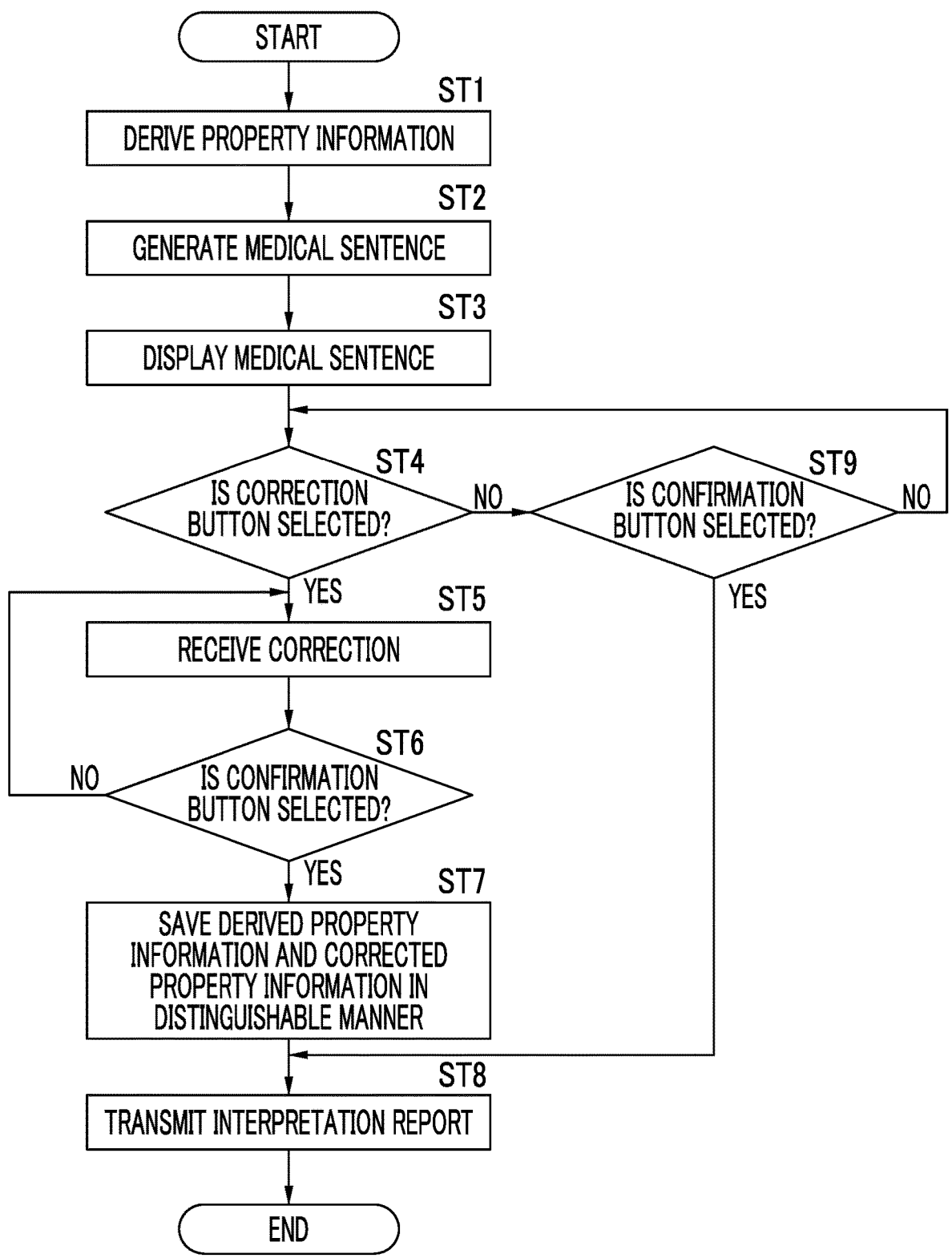
FIG. 11 is a flowchart showing an information saving process performed in the present embodiment.

Next, a process performed in the present embodiment will be described. FIG. 11 is a flowchart showing an information saving process performed in the present embodiment. It is assumed that the medical image to be interpreted is acquired from the image server 5 by the image acquisition unit 21 and is saved in the storage 13. The process is started in a case where an instruction to create an interpretation report is given by the radiologist, and the analysis unit 22 analyzes the medical image to derive property information indicating the property of the structure of interest such as an abnormal shadow candidate included in the medical image (Step ST1). Next, the analysis record generation unit 23 generates a medical sentence related to the medical image based on the property information as an image analysis record (Step ST2). Then, the display control unit 24 displays the medical sentence generated by the analysis record generation unit 23 on the sentence display region 52 of the display screen 50 displayed on the display 14 (Step ST3).

Next, the display control unit 24 determines whether or not the correction button 58A displayed on the display screen 50 is selected (Step ST4). In a case where Step ST4 is affirmative, the correction unit 25 receives the correction of the property information included in the medical sentence displayed in the sentence display region 52 using the input device 15 (Step ST5). Subsequently, the correction unit 25 determines whether or not the confirmation button 58B is selected (Step ST6). In a case where Step ST6 is negative, the process returns to Step ST5 and the correction is continuously received. In a case where Step ST6 is affirmative, the save control unit 26 saves the derived property information and the corrected property information in the storage 13 in a distinguishable manner (Step ST7). Then, the display control unit 24 transcribes the corrected medical sentence to the interpretation report, the communication unit 27 transmits the interpretation report to which the corrected medical sentence is transcribed to the report server 7 together with the slice image SL1 (transmission of interpretation report: Step ST8), and the process ends.

On the other hand, in a case where Step ST4 is negative, the display control unit 24 determines whether or not the confirmation button 58B is selected (Step ST9). In a case where Step ST9 is negative, the process returns to Step ST4. In a case where Step ST9 is affirmative, the process proceeds to Step ST8, the display control unit 24 transcribes the medical sentence to the interpretation report, the communication unit 27 transmits the interpretation report to which the medical sentence is transcribed to the report server 7 together with the slice image SL1, and the process ends.

Figure 12:
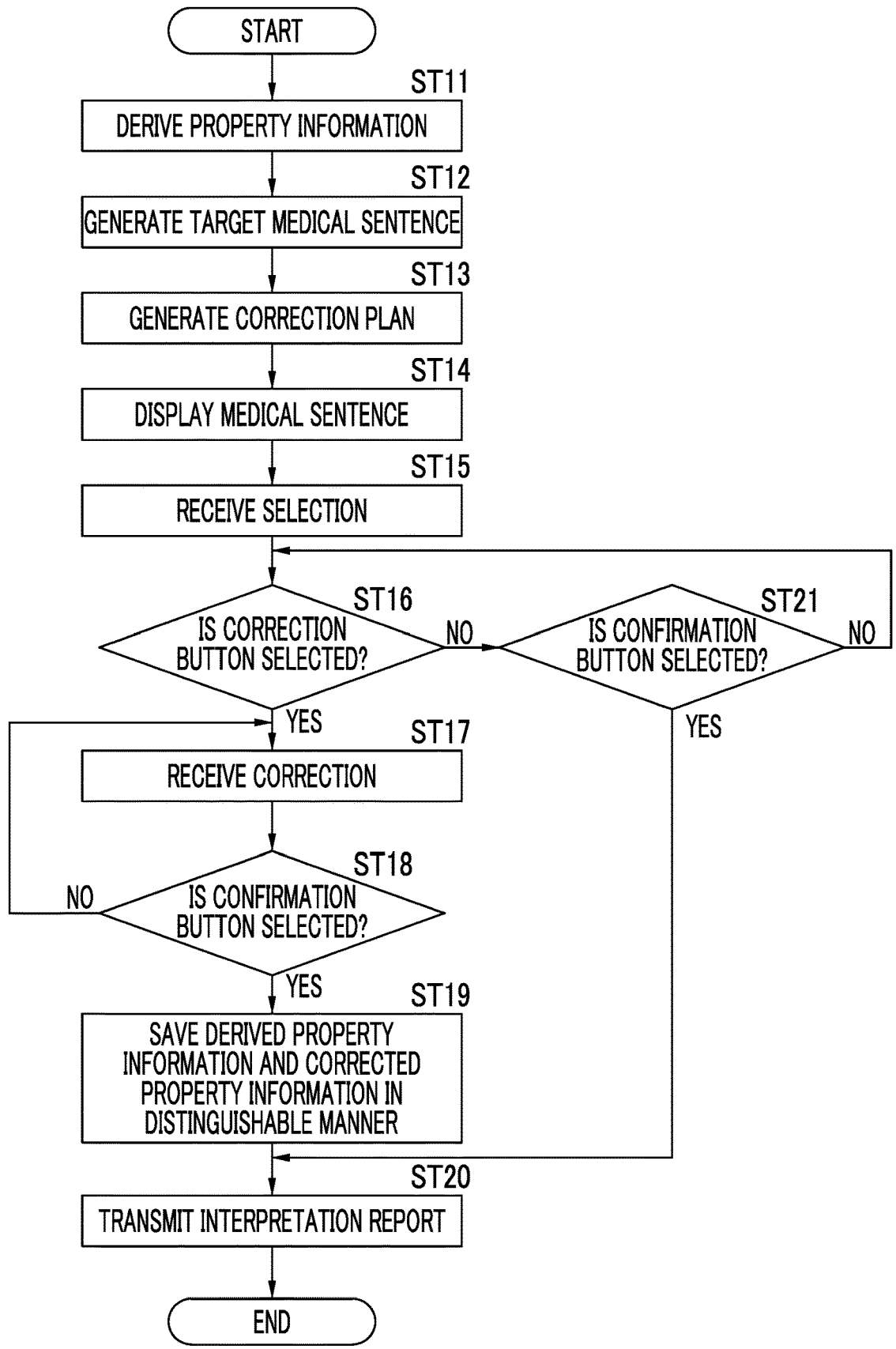
FIG. 12 is a flowchart showing an analysis record generation process performed in the present embodiment.

Next, a process performed in a case where the saved information in which the derived property information and the corrected property information are saved in a distinguishable manner is saved in the storage 13 will be described. FIG. 12 is a flowchart showing an analysis record generation process performed in the present embodiment. It is assumed that the medical image to be interpreted is acquired from the image server 5 by the image acquisition unit 21 and is saved in the storage 13. Further, it is assumed that the saved information 45 in which the derived property information and the corrected property information are saved in a distinguishable manner is also saved in the storage 13.

The process is started in a case where an instruction to create an interpretation report is given by the radiologist, and the analysis unit 22 analyzes the medical image to derive property information indicating the property of the structure of interest such as an abnormal shadow candidate included in the medical image (Step ST11). Next, the analysis record generation unit 23 generates a target medical sentence regarding the target medical image as an image analysis record based on the property information derived by the analysis unit 22 without reference to the saved information 45, that is, without referring to the saved information 45 (Step ST12). Further, the analysis record generation unit 23 refers to the saved information 45 saved in the report server 7 and generates a target medical sentence regarding the target medical image as an alternative plan (Step ST13). Then, the display control unit 24 displays the target medical sentence 75 and the alternative plan 76 generated by the analysis record generation unit 23 on the sentence display region 52 of the display screen 50 displayed on the display 14 (display of medical sentence: Step ST14).

Next, the display control unit 24 receives the selection of either the target medical sentence 75 or the alternative plan 76 (Step ST15). Further, the display control unit 24 determines whether or not the correction button 78A displayed on the display screen is selected (Step ST16). In a case where Step ST16 is affirmative, the correction unit 25 receives the correction of the property information included in the selected medical sentence using the input device 15 (Step ST17). Subsequently, the correction unit 25 determines whether or not the confirmation button 78B is selected (Step ST18). In a case where Step ST18 is negative, the process returns to Step ST17 and the correction is continuously received. In a case where Step ST18 is affirmative, the save control unit 26 saves the derived property information and the corrected property information in the storage 13 in a distinguishable manner (Step ST19). Then, the display control unit 24 transcribes the selected and corrected medical sentence to the interpretation report, the communication unit 27 transmits the interpretation report to which the medical sentence is transcribed to the report server 7 together with the slice image SL1 (transmission of interpretation report: Step ST20), and the process ends.

On the other hand, in a case where Step ST16 is negative, the display control unit 24 determines whether or not the confirmation button 78B is selected (Step ST21). In a case where Step ST21 is negative, the process returns to Step ST16. In a case where Step ST21 is affirmative, the process proceeds to Step ST20, the display control unit 24 transcribes the selected medical sentence to the interpretation report, the communication unit 27 transmits the interpretation report to which the medical sentence is transcribed to the report server 7 together with the slice image SL1, and the process ends.

In this way, in the present embodiment, a plurality of pieces of property information indicating the properties of the structure of interest included in the image are derived, an image analysis record including at least a portion of the plurality of pieces of property information is generated, a correction of the property information by a user is received, and the derived property information and the corrected property information are saved in a distinguishable manner. Therefore, by referring to the saved information that has been saved, it is possible to recognize which of property information derived by analyzing an image has been corrected in a case where an image analysis record generated from the image has been corrected.

In addition, regarding the target medical image, in addition to the target medical sentence generated based on the property information derived from the target medical image without referring to the saved information 45, by displaying an alternative plan that refers to the saved information, it is possible to increase the choices of sentences to be transcribed in the interpretation report. Therefore, the radiologist can transcribe the medical sentence describing the desired property information into the interpretation report.

Although the target medical sentence is generated using only the property information derived by the analysis unit 22 for the target medical image in the above embodiment, the present disclosure is not limited thereto. An alternative plan generated by referring only to the saved information 45 may be used as the target medical sentence without generating the target medical sentence using only the property information derived by the analysis unit 22 for the target medical image.

Figure 13:
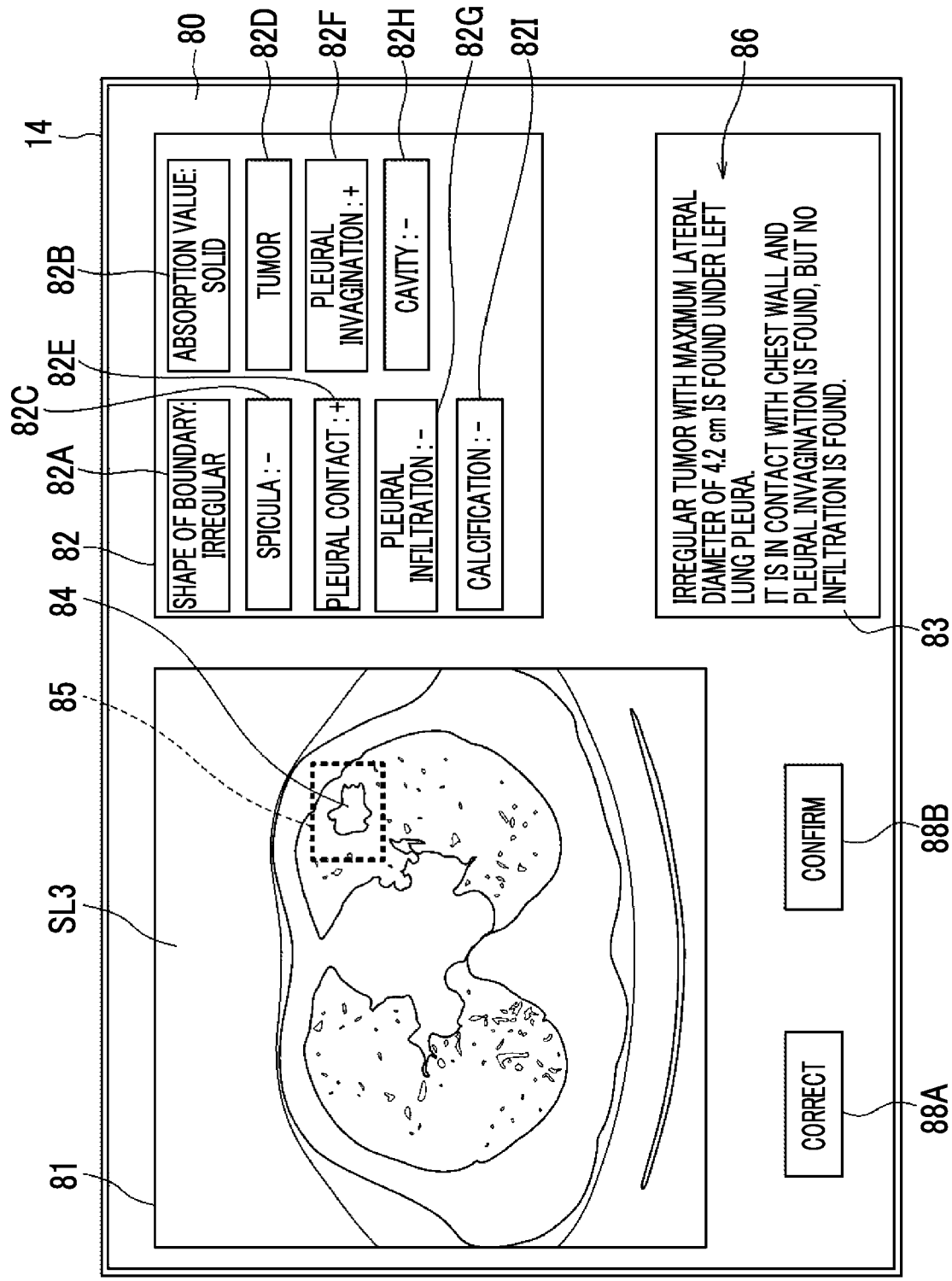
FIG. 13 is a diagram showing an example of a display screen of a medical sentence and a collation result.

Although the medical sentence 55 displayed in the sentence display region 52 of the display screen 50 is corrected by using the input device 15 in the above embodiment, the present disclosure is not limited thereto. FIG. 13 is a diagram showing another example of a display screen of a medical sentence according to the present embodiment. As shown in FIG. 13, a display screen 80 includes an image display region 81, a property information display region 82, and a sentence display region 83. In the image display region 81, a slice image SL3 that is most likely to specify the abnormal shadow candidate detected by the analysis unit 22 is displayed. The slice image SL3 includes an abnormal shadow candidate 84, and the abnormal shadow candidate 84 is surrounded by a rectangular region 85.

In the property information display region 82, buttons 82A to 82I for respectively designating the shape of the boundary (clear and irregular), the type of absorption value (solid type and frosted glass type), the presence or absence of spicula, whether it is a tumor or a nodule, the presence or absence of pleural contact, the presence or absence of pleural invagination, the presence or absence of pleural infiltration, the presence or absence of a cavity, and the presence or absence of calcification are displayed.

In the sentence display region 83, a medical sentence 86 generated by the analysis record generation unit 23 is displayed. The medical sentence 86 is "An irregular tumor with a maximum lateral diameter of 4.2 cm is found under the left lung pleura. It is in contact with the chest wall and pleural invagination is found, but no infiltration is found." The property information used in the medical sentence 86 is "under left lung pleura", "irregular", "4.2 cm", "tumor", "with chest wall contact", "with pleural invagination", and "no pleural infiltration" among the property information derived by the analysis unit 22.

Note that, below the image display region 81, a correction button 88A and a confirmation button 88B are displayed. The functions of the correction button 88A and the confirmation button 88B are the same as those of the correction buttons 58A and 78A and the confirmation buttons 58B and 78B described above, and detailed description thereof will be thus omitted here.

The radiologist can correct the medical sentence 86 by selecting a desired button for the property information displayed in the property information display region 82. For example, by selecting the button 82C, it is possible to correct "no spicula" to "with spicula". Further, by selecting the button 82E, it is possible to correct "with pleural contact" to "no pleural contact". As a result, in the sentence display region 83, the corrected medical sentence of "A tumor having an irregular shape and spicula and a maximum lateral diameter of 4.2 cm is found under the left lung pleura. Pleural invagination is found, but no infiltration is found" is displayed.

By correcting the property information included in the medical sentence on the display screen in this way, it becomes possible to save the derived property information and the corrected property information as in the above embodiment in a distinguishable manner.

Also, in the above embodiments, the creation support process for the medical document such as the interpretation report is performed by generating the medical sentence using the medical image with the lung as the diagnosis target, but the diagnosis target is not limited to the lung. In addition to the lung, any part of a human body such as a heart, liver, brain, and limbs can be diagnosed. In this case, for each learning model of the analysis unit 22 and the analysis record generation unit 23, learning models that perform the analysis process and the analysis record process according to the diagnosis target are prepared, a learning model that performs the analysis process and the analysis record generation process according to the diagnosis target is selected, and a process of generating an analysis record is executed.

In addition, although the technique of the present disclosure is applied to the case of creating an interpretation report as an analysis record in the above embodiments, the technique of the present disclosure can also be applied to a case of creating medical documents other than the interpretation report, such as an electronic medical record and a diagnosis report, as an analysis record.

Further, although the image analysis record is generated using the medical image in the above embodiment, the present disclosure is not limited thereto. Of course, the technology of the present disclosure can also be applied even in a case where an image analysis record targeting any image other than a medical image is generated. For example, the technique of the present disclosure can be applied even in a case where the image of the chemical formula of the compound is analyzed, the type of cyclic hydrocarbon and the type of functional group are derived as property information, and the name of the compound is generated as an image analysis record from the derived property information.

Further, in each of the above embodiments, for example, as hardware structures of processing units that execute various kinds of processing, such as the image acquisition unit 21, the analysis unit 22, the analysis record generation unit 23, the display control unit 24, the correction unit 25, the save control unit 26, and the communication unit 27, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are composed of one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. An information saving apparatus comprising at least one processor,
    wherein the processor is configured to
    analyze an image to derive a plurality of pieces of property information indicating properties of a structure of interest included in the image,
    generate an image analysis record including at least a portion of the plurality of pieces of property information, wherein the portion of the plurality of pieces of property information included in the image analysis record comprises first property information and second property information,
    receive a correction of the first property information in the image analysis record by a user, and
    save the second property information and the corrected first property information as saved information in a distinguishable manner.

2. The information saving apparatus according to claim 1, wherein the processor is configured to display the image analysis record on a display.

3. The information saving apparatus according to claim 2, wherein the processor is configured to receive at least one of deletion of the first property information included in the displayed image analysis record or addition of the first property information not included in the image analysis record as the correction.

4. The information saving apparatus according to claim 2, wherein the processor is configured to
    display an entirety or a portion of the plurality of pieces of property information on the display, and
    receive the correction based on selection of the first property information by the user.

5. The information saving apparatus according to claim 1, further comprising a learning model trained to output the image analysis record in a case where at least a portion of the plurality of pieces of property information is input.

6. The information saving apparatus according to claim 1, wherein the processor is configured to generate a sentence including at least a portion of the plurality pieces of the property information as the image analysis record.

7. The information saving apparatus according to claim 6, wherein the image is a medical image, and the sentence is a medical sentence related to the structure of interest included in the medical image.

8. The information saving apparatus according to claim 1,
    wherein a first flag and a second flag are respectively given to the corrected first property information and the second property information in the saved information,
    wherein the first flag indicates that a correction has been subject to the first property information, and
    wherein the second flag indicates that no correction has been subject to the second property information.

9. An analysis record generation apparatus comprising at least one processor,
    wherein the processor is configured to
    derive a plurality of pieces of property information indicating properties of a structure of interest included in a target image to be analyzed, and
    refer to the saved information saved by the information saving apparatus according to claim 1 to generate a target image analysis record including at least a portion of the plurality of pieces of the property information.

10. The analysis record generation apparatus according to claim 9, wherein the processor is configured to
    specify the saved information including property information that matches the property information derived from the target image, and
    generate an image analysis record associated with the specified saved information as the target image analysis record.

11. The analysis record generation apparatus according to claim 9, wherein the processor is further configured to generate another target image analysis record including at least a portion of the plurality of pieces of property information without reference to the saved information.

12. The analysis record generation apparatus according to claim 11, wherein the processor is configured to display the target image analysis record and the other target image analysis record on a display.

13. The analysis record generation apparatus according to claim 12, wherein the processor is configured to receive selection of either the displayed target image analysis record or the displayed other target image analysis record.

14. The analysis record generation apparatus according to claim 9, wherein the processor is configured to generate a sentence including at least a portion of the plurality of pieces of property information as the target image analysis record.

15. The analysis record generation apparatus according to claim 14, wherein the image is a medical image, and the sentence is a medical sentence related to the structure of interest included in the medical image.

16. An analysis record generation method comprising:
    deriving a plurality of pieces of property information indicating properties of a structure of interest included in a target image to be analyzed; and
    referring to the saved information saved by the information saving apparatus according to claim 1 to generate a target image analysis record including at least a portion of the plurality of pieces of property information.

17. A non-transitory computer-readable storage medium that stores an analysis record generation program for causing a computer to execute a procedure comprising:

deriving a plurality of pieces of property information indicating properties of a structure of interest included in a target image to be analyzed; and referring to the saved information saved by the information saving apparatus according to claim 1 to generate a target image analysis record including at least a portion of the plurality of pieces of property information.

18. An information saving method comprising:

analyzing an image to derive a plurality of pieces of property information indicating properties of a structure of interest included in the image;

generating an image analysis record including at least a portion of the plurality of pieces of property information, wherein the portion of the plurality of pieces of property information included in the image analysis record comprises first property information and second property information;

receiving a correction of the first property information in the image analysis record by a user; and saving the second property information and the corrected first property information as saved information in a distinguishable manner.

19. A non-transitory computer-readable storage medium that stores an information saving program for causing a computer to execute a procedure comprising:

analyzing an image to derive a plurality of pieces of property information indicating properties of a structure of interest included in the image;

generating an image analysis record including at least a portion of the plurality of pieces of property information, wherein the portion of the plurality of pieces of property information included in the image analysis record comprises first property information and second property information;

receiving a correction of the first property information in the image analysis record by a user; and saving the second property information and the corrected first property information as saved information in a distinguishable manner.

\* \* \* \* \*